United States Patent
Kojima et al.

(10) Patent No.: US 10,705,045 B2
(45) Date of Patent: Jul. 7, 2020

(54) GAS SENSOR ELEMENT AND METHOD FOR PRODUCING GAS SENSOR ELEMENT

(71) Applicant: NGK SPARK PLUG CO., LTD., Nagoya-shi, Aichi (JP)

(72) Inventors: Akinori Kojima, Ichinomiya (JP); Hitoshi Furuta, Tajimi (JP)

(73) Assignee: NGK SPARK PLUG CO., LTD., Aichi (JP)

( * ) Notice: Subject to any disclaimer, the term of this patent is extended or adjusted under 35 U.S.C. 154(b) by 110 days.

(21) Appl. No.: 15/665,499

(22) Filed: Aug. 1, 2017

(65) Prior Publication Data
US 2018/0038821 A1 Feb. 8, 2018

(30) Foreign Application Priority Data
Aug. 3, 2016 (JP) .................. 2016-153021

(51) Int. Cl.
| | | |
|---|---|---|
| *G01N 27/26* | (2006.01) | |
| *G01N 27/407* | (2006.01) | |
| *G01N 27/419* | (2006.01) | |
| *G01N 27/417* | (2006.01) | |
| *G01N 33/00* | (2006.01) | |

(52) U.S. Cl.
CPC ..... *G01N 27/4075* (2013.01); *G01N 27/4074* (2013.01); *G01N 27/4077* (2013.01); *G01N 27/417* (2013.01); *G01N 27/419* (2013.01); *G01N 33/0027* (2013.01)

(58) Field of Classification Search
CPC ........... G01N 27/4074; G01N 27/4075; G01N 27/4077; G01N 27/417; G01N 27/419; G01N 27/41; G01N 33/0027

USPC .......................................................... 204/424
See application file for complete search history.

(56) References Cited

U.S. PATENT DOCUMENTS

| | | | | |
|---|---|---|---|---|
| 3,914,169 A | * | 10/1975 | Horowitz | G01N 27/4075 204/427 |
| 2005/0263396 A1 | * | 12/2005 | Naito | G01N 27/4071 204/424 |
| 2006/0180195 A1 | * | 8/2006 | Luch | H01L 31/0392 136/244 |

(Continued)

FOREIGN PATENT DOCUMENTS

| | | | | |
|---|---|---|---|---|
| JP | 2005-338091 | * | 12/2005 | ......... G01N 27/4071 |
| JP | 2015-059758 A | | 3/2015 | |

OTHER PUBLICATIONS

Translation of JP 2005-338091, 2005, pp. 1-11 (Year: 2005).*

*Primary Examiner* — Thanh Truc Trinh
(74) *Attorney, Agent, or Firm* — Sughrue Mion, PLLC (57) ABSTRACT

A gas sensor element including a lead portion (79a) formed on a lower surface of an insulating member (76) and extending through a through hole (176) to an upper surface thereof, and a lead portion (79b) extending from the upper surface of the insulating member (76) through the through hole (176) to the lower surface of the insulating member (76) so as to cover the lead portion (79a) along the inner circumferential wall and a portion of the lower surface around the through hole. The lead portion (79a) has a section exposed to a space (230) on the lower surface side of the insulating member (76). The lead portion (79b) is disposed so as to face the insulating member (76) with the space (230) therebetween. The lead portion (79a) communicates with the outside through the space (230). Also disclosed is a method for producing the gas sensor element.

17 Claims, 4 Drawing Sheets

(56) References Cited

U.S. PATENT DOCUMENTS

2015/0075254 A1  3/2015  Sakuma et al.

* cited by examiner

GAS SENSOR ELEMENT AND METHOD FOR PRODUCING GAS SENSOR ELEMENT

BACKGROUND OF THE INVENTION

1. Field of the Invention

The present disclosure relates to a gas sensor element that detects the concentration of a specific component contained in a gas under measurement and to a method for producing the gas sensor element.

2. Description of the Related Art

A gas sensor element disclosed in Patent Document 1 includes an oxygen concentration detection cell composed of an oxygen ion-conductive solid electrolyte body and a pair of electrodes including a detection electrode and a reference electrode that are formed so as to sandwich the solid electrolyte body therebetween. The oxygen concentration detection cell generates an electromotive force corresponding to the difference in oxygen concentration between the detection electrode and the reference electrode.

[Patent Document 1] Japanese Patent Application Laid-Open (kokai) No. 2015-59758

3. Problems to be Solved by the Invention

Oxygen stored in the reference electrode is discharged through a reference electrode lead connected to the reference electrode. In this case, if the flow path of the oxygen is blocked in the vicinity of a through hole connected to the reference electrode lead, the amount of oxygen discharged through the through hole decreases. This makes it difficult to maintain the oxygen concentration in the reference electrode constant, and as a result, the characteristics of the gas sensor element may become unstable.

SUMMARY OF THE INVENTION

It is therefore an object of the present disclosure to improve the stability of the characteristics of a gas sensor element.

The above object has been achieved by providing, in a first aspect of the present disclosure (1), a gas sensor element comprising a measurement chamber, a pumping cell, an oxygen concentration detection cell, a first lead portion, and a second lead portion.

A gas under measurement is introduced into the measurement chamber. The pumping cell includes a first solid electrolyte body having oxygen ion conductivity and a pair of pumping electrodes formed on the first solid electrolyte body. The pumping cell pumps oxygen into or out of the gas under measurement that has been introduced into the measurement chamber when a pumping current flows between the pair of pumping electrodes.

The oxygen concentration detection cell includes a plate-shaped cell member formed into a plate shape and including at least a second solid electrolyte body having oxygen ion conductivity, a detection electrode, and a reference electrode having oxygen permeability. The detection electrode is exposed to the measurement chamber, and the oxygen concentration detection cell generates an electromotive force corresponding to a difference in oxygen concentration between the detection electrode and the reference electrode. The detection electrode is formed on an upper surface of the second solid electrolyte body. The reference electrode is formed on a lower surface of the second solid electrolyte body.

A first lead portion having oxygen permeability is formed on a lower surface of the plate-shaped cell member so as to extend from the reference electrode to a through hole formed in the plate-shaped cell member and further extend from the lower surface of the plate-shaped cell member through the through hole to an upper surface of the plate-shaped cell member so as to cover an inner circumferential wall of the through hole and a portion of the upper surface around the through hole.

A second lead portion is formed so as to extend from the upper surface of the plate-shaped cell member through the through hole to the lower surface of the plate-shaped cell member so as to cover the first lead portion along the inner circumferential wall of the through hole and a portion of the lower surface around the through hole.

The gas sensor element of the present disclosure (1) further comprises an insulating layer. The insulating layer is disposed below the plate-shaped cell member so as to face the plate-shaped cell member and thereby form a space along the lower surface of the plate-shaped cell member extending across the through hole and a periphery of the through hole. Further, the first lead portion has a section exposed to the space below the lower surface of the plate-shaped cell member, and the second lead portion is spaced apart from the insulating layer with the space therebetween. The first lead portion is in communication with the outside of the gas sensor element through the space.

In the gas sensor element of the present disclosure (1) configured as described above, the first lead portion has a section exposed to the space. Therefore, oxygen stored in the reference electrode can be released to the space through the first lead portion connected to the reference electrode. Further, the second lead portion is spaced apart from the insulating layer. Therefore, the oxygen released from the first lead portion to the space can flow to the through hole and can be discharged to the outside of the gas sensor element through the through hole.

Thus, the gas sensor element of the present disclosure (1) can prevent a decrease in the amount of oxygen discharged through the through hole. Therefore, the gas sensor element of the present disclosure (1) can suppress fluctuations in the oxygen concentration in the reference electrode, to thereby improve the stability of the characteristics of the gas sensor element.

In a second aspect, the present disclosure provides (2) a method for producing a gas sensor element including a measurement chamber, a pumping cell, and an oxygen concentration detection cell.

In the gas sensor element production method of the present disclosure (2), a wiring pattern for a first lead portion having oxygen permeability and extending from the reference electrode to a through hole formed in the plate-shaped cell member is printed on a lower surface of the plate-shaped cell member, while vacuum drawing is carried out, such that a gas flows from a lower side of the plate-shaped cell member to an upper side of the plate-shaped cell member through the through hole.

In the gas sensor element production method of the present disclosure, a wiring pattern for a first lead portion having oxygen permeability and extending from the reference electrode to a through hole formed in the plate-shaped cell member is printed on a lower surface of the plate-shaped cell member, while vacuum drawing is carried out, such that a gas flows from the upper side of the plate-shaped cell member to the lower side of the plate-shaped cell member through the through hole.

In the gas sensor element production method of the present disclosure (2), a heat-decomposable paste is printed on an upper surface of a lower insulating layer that is disposed below the plate-shaped cell member so as to face the plate-shaped cell member. The heat-decomposable paste is disposed in a through hole-facing region that faces the through hole and in a periphery of the through hole-facing region.

In the gas sensor element production method (2) of the present disclosure, an alumina paste is printed on the upper surface of the lower insulating layer. The alumina paste is disposed in a region other than a region in which the heat-decomposable paste has been disposed.

In the gas sensor element production method (2) of the present disclosure, the plate-shaped cell member is stacked on the upper surface of the lower insulating layer.

The gas sensor element production method of the present disclosure (2) described above is a method for producing the gas sensor element of the above-described aspect of the present disclosure (1). With this method, the same effects as those of the gas sensor element of the above-described aspect of the present disclosure (1) can be obtained.

DESCRIPTION OF REFERENCE NUMERALS

Reference numerals used to identify various features in the drawings include the following.

7: gas sensor element, 75, 83: solid electrolyte body, 76: insulating member, 77, 79, 85, 87: porous electrode, 79a: lead portion, 79b: output-extracting lead portion, 81: oxygen concentration detection cell, 89: oxygen pump cell, 91: gas measurement chamber, 101: insulating substrate, 176: through hole, 210: carbon paste, 220: insulating layer, 230: space

DETAILED DESCRIPTION OF THE PREFERRED EMBODIMENTS

The present disclosure will next be described with reference to the drawings. However, the present disclosure should not be construed as being limited thereto.

A gas sensor 1 of one embodiment is an oxygen sensor attached to an exhaust pipe of an internal combustion engine and used to measure the concentration of oxygen in exhaust gas.

Figure 1:
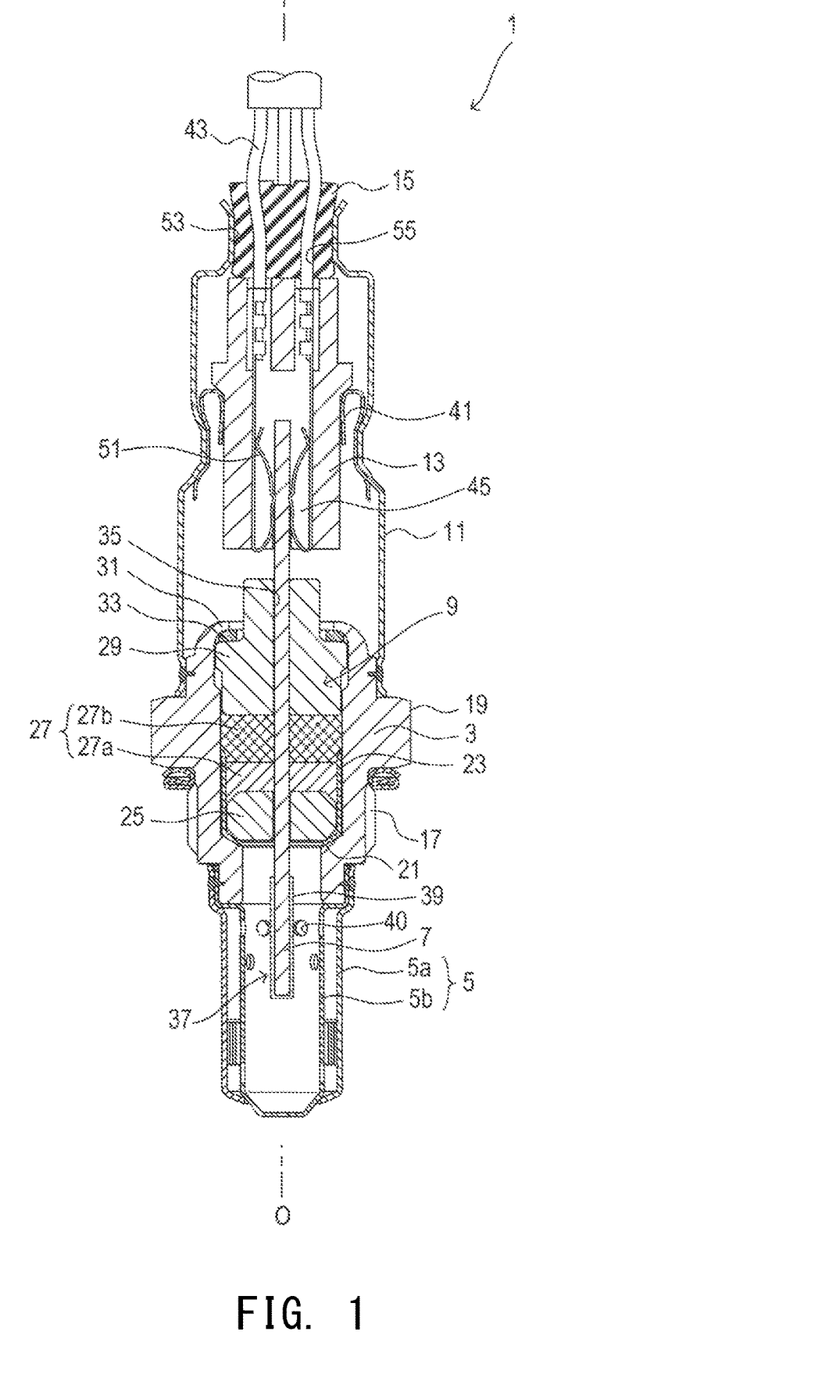
FIG. 1 is a cross-sectional view of a gas sensor 1.

As shown in FIG. 1, the gas sensor 1 mainly includes a metallic shell 3, a protector 5, a gas sensor element 7, a holding section 9, an outer tube 11, a separator 13, and a rubber cap 15.

The metallic shell 3 is a tubular member made of a heat-resistant metal such as stainless steel. The metallic shell 3 has, on its outer circumference, a male threaded portion 17 for attaching the gas sensor 1 to the exhaust pipe and a hexagonal portion 19 for engaging an attachment tool when the gas sensor 1 is attached to the exhaust pipe. The metallic shell 3 further has a shell-side step portion 21 protruding radially inward.

The holding section 9 is disposed inside the metallic shell 3 and holds the gas sensor element 7. The holding section 9 includes, from its forward end side, a metallic holder 23 supported by the shell-side step portion 21 and holds the gas sensor element 7, a ceramic holder 25 disposed inside the metallic holder 23 and used to place the gas sensor element 7 at a prescribed position, talc 27, and a ceramic sleeve 29 disposed on the talc 27.

The talc 27 includes first talc 27a and second talc 27b. The first talc 27a is compressed and packed inside the metallic holder 23 to ensure hermetic sealing between the inner surface of the metallic holder 23 and the outer surface of the gas sensor element 7. The second talc 27b is compressed and packed on the first talc 27a to ensure hermetic sealing between the inner surface of the metallic shell 3 and the outer surface of the gas sensor element 7.

A crimp portion 31 located at the rear end of the metallic shell 3 is folded inward, and the ceramic sleeve 29 is thereby pressed toward the forward end of the metallic shell 3 through a stainless steel-made ring member 33.

An axial hole 35 extending along an axial line O is formed in the ceramic sleeve 29 and the ceramic holder 25, and the gas sensor element 7 is inserted into the ceramic sleeve 29 and the ceramic holder 25 (i.e., the holding section 9).

The gas sensor element 7 is an elongated plate-shaped member extending in the vertical direction in FIG. 1 (i.e., has rectangular principal and side surfaces). The gas sensor element 7 is held by the holding section 9 along the center axis of the metallic shell 3 such that the forward end of the gas sensor element 7 protrudes from the forward end of the metallic shell 3 and the rear end of the gas sensor element 7 protrudes from the rear end of the metallic shell 3.

A coating layer 39, which is a porous protective layer, is formed so as to cover a forward end portion 37 of the gas sensor element 7.

The protector 5 is a metallic tubular member that has a plurality of gas inlets 40 and covers the forward end portion 37 of the gas sensor element 7 protruding from the forward end of the metallic shell 3. The protector 5 is welded to the outer circumference of the forward end of the metallic shell 3.

The protector 5 has a double structure including a closed-end cylindrical outer protector 5a disposed on the outer side and a closed-end cylindrical inner protector 5b disposed on the inner side. A forward end portion of the inner protector 5b protrudes from the forward end of the outer protector 5a.

The outer tube 11 is a metallic member laser-welded to the metallic shell 3 with a rear end portion of the metallic shell 3 fitted into a forward opening of the outer tube 11, and the separator 13 is disposed inside a rear end portion of the outer tube 11.

The separator 13 is a tubular member made of an electrically insulating ceramic and is held by an elastic holding member 41 disposed in a gap between the separator 13 and the outer tube 11.

The separator 13 has through holes 45 into which a plurality of lead wires 43 electrically connected to the gas sensor element 7 are inserted. A plurality of connection terminals 51 for establishing electrical connection between the gas sensor element 7 and the lead wires 43 are disposed in the through holes 45.

The rubber cap 15 is a generally cylindrical member for closing a rear opening 53 of the outer tube 11. The rubber cap 15 also has a plurality of through holes 55 into which the lead wires 43 are inserted.

Figure 2:
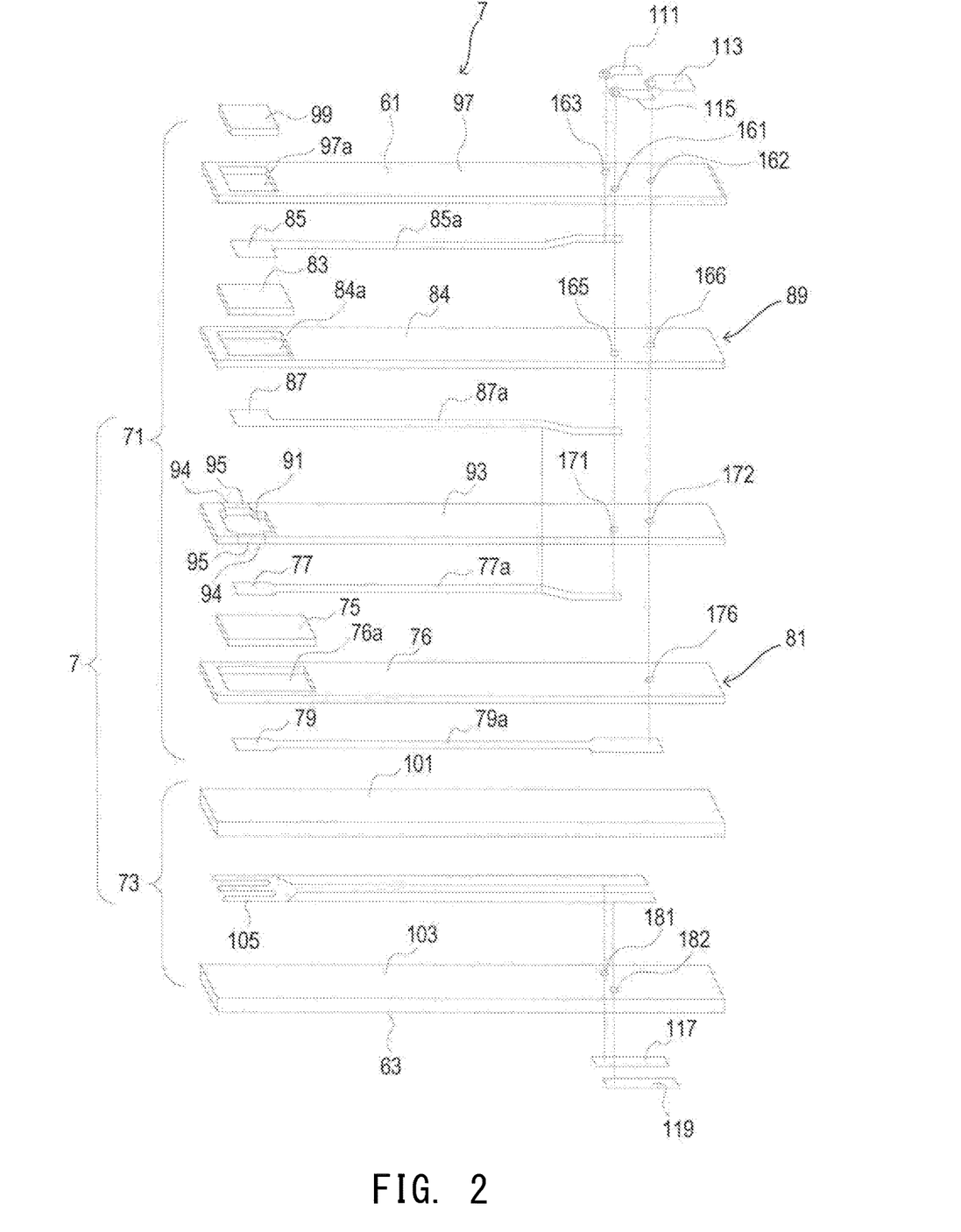
FIG. 2 is an exploded perspective view of a gas sensor element 7.

As shown in FIG. 2, the gas sensor element 7 is an elongated rectangular cuboidal member and is a stacked body including a plate-shaped detection element 71 and a plate-shaped heater element 73 stacked one on another.

The detection element 71 includes an oxygen concentration detection cell 81, an oxygen pump cell 89, an insulating spacer 93, and an insulating substrate 97.

The oxygen concentration detection cell 81 includes an insulating member 76, a solid electrolyte body 75, a porous electrode 77, a lead portion 77a, a porous electrode 79, and a lead portion 79a.

The insulating member 76 is a plate-shaped member formed mainly of alumina and has a through hole 76a extending in the thickness direction of the insulating member 76. The solid electrolyte body 75 is disposed within the through hole 76a of the insulating member 76. The porous electrodes 77 and 79 forming a pair are disposed on the upper and lower surfaces, respectively, of the solid electrolyte body 75 so as to sandwich the solid electrolyte body 75.

The lead portion 77a is connected at one end to the porous electrode 77 and is disposed so as to extend in the lengthwise direction (i.e., the left-right direction in FIG. 2) of the gas sensor element 7. The lead portion 79a is connected at one end to the porous electrode 79 and is disposed so as to extend in the lengthwise direction of the gas sensor element 7.

The oxygen pump cell 89 includes an insulating member 84, a solid electrolyte body 83, a porous electrode 85, a lead portion 85a, a porous electrode 87, and a lead portion 87a.

The insulating member 84 is a plate-shaped member formed mainly of alumina and has a through hole 84a extending in the thickness direction of the insulating member 84. The solid electrolyte body 83 is disposed within the through hole 84a of the insulating member 84. The porous electrodes 85 and 87 forming a pair are disposed on the upper and lower surfaces, respectively, of the solid electrolyte body 83 so as to sandwich the solid electrolyte body 83.

The lead portion 85a is connected at one end to the porous electrode 85 and disposed so as to extend in in the lengthwise direction of the gas sensor element 7. The lead portion 87a is connected at one end to the porous electrode 87 and disposed so as to extend in the lengthwise direction of the gas sensor element 7.

The solid electrolyte bodies 75 and 83 are formed of zirconia in which yttria is dissolved as a stabilizer. The cross-sectional area of the solid electrolyte body 75 in a plane perpendicular to the stacking direction is larger than the cross-sectional area of the solid electrolyte body 83.

The porous electrodes 77, 79, 85, and 87 and the lead portions 77a, 79a, 85a, and 87a are formed mainly of Pt.

The insulating spacer 93 is a plate-shaped member formed mainly of alumina and includes a hollow gas measurement chamber 91. The insulating spacer 93 is stacked between the oxygen concentration detection cell 81 and the oxygen pump cell 89. The porous electrode 77 of the oxygen concentration detection cell 81 and the porous electrode 87 of the oxygen pump cell 89 are disposed so as to be exposed to the interior of the gas measurement chamber 91.

Two gas introduction ports 94 serving as exhaust gas inlets are formed on side surfaces of the insulating spacer 93. The gas introduction ports 94 are connected to the gas measurement chamber 91. Diffusion controlling sections 95 are formed in paths extending from the two gas introduction ports 94 to the gas measurement chamber 91. The diffusion controlling sections 95 are formed from a porous material made of, for example, alumina and control the rate of flow of exhaust gas into the gas measurement chamber 91. The diffusion controlling sections 95 are disposed such that parts thereof are exposed at the gas introduction ports 94.

The insulating substrate 97 is a plate-shaped member formed mainly of alumina and has a space 97a extending through the insulating substrate 97 in its thickness direction. A gas passage member 99 formed of the same porous material as the material of the diffusion controlling sections 95 is embedded in the space 97a of the insulating substrate 97. The porous electrode 85 of the oxygen pump cell 89 is exposed to the exhaust gas through the gas passage member 99. The gas measurement chamber 91 is formed so as to be located on the forward end side of the gas sensor element 7 (i.e., the left side in FIG. 2).

The heater element 73 includes insulating substrates 101 and 103 formed mainly of alumina and a heat-generating resistor pattern 105 formed mainly of Pt and sandwiched between the insulating substrates 101 and 103.

Three electrode pads 111, 113, and 115 are formed in a rear end portion (i.e., the right side in FIG. 2) of a first principal surface 61 of the gas sensor element 7, and two electrode pads 117 and 119 are formed in a rear end portion of a second principal surface 63 of the gas sensor element 7.

The electrode pad 115 is electrically connected to the porous electrode 77 of the oxygen concentration detection cell 81 through a through hole 161 formed in the insulating substrate 97, a through hole 165 formed in the insulating member 84, a through hole 171 formed in the insulating spacer 93, and the lead portion 77a. The electrode pad 115 is also electrically connected to the porous electrode 87 of the oxygen pump cell 89 through the through hole 161 formed in the insulating substrate 97, the through hole 165 formed in the insulating member 84, and the lead portion 87a. Therefore, the porous electrode 77 and the porous electrode 87 are electrically connected together so as to be maintained at the same potential. A conductor is disposed in each of the through holes (i.e., the through holes 161 and 165 etc.).

The electrode pad 113 is electrically connected to the porous electrode 79 of the oxygen concentration detection cell 81 through a through hole 162 formed in the insulating substrate 97, a through hole 166 formed in the insulating member 84, a through hole 172 formed in the insulating spacer 93, a through hole 176 formed in the insulating member 76, and the lead portion 79a. The electrode pad 111 is electrically connected to the porous electrode 85 of the oxygen pump cell 89 through a through hole 163 formed in the insulating substrate 97 and the lead portion 85a.

The electrode pads 117 and 119 are electrically connected to opposite ends of the heat-generating resistor pattern 105 through through holes 181 and 182 formed in the insulating substrate 103.

Next, a method for measuring the concentration of oxygen using the gas sensor 1 will be described.

A sensor controller connected to the gas sensor 1 first supplies a voltage across the heat-generating resistor pattern 105 to generate heat from the heater element 73, and the oxygen concentration detection cell 81 and the oxygen pump cell 89 are thereby heated.

Then the sensor controller supplies a small current Icp flowing from the porous electrode 79 of the oxygen concentration detection cell 81 to the porous electrode 77. Oxygen ions thereby move toward the porous electrode 79, so that an oxygen atmosphere whose oxygen concentration serves as a reference for gas detection is generated in the porous electrode 79. In this manner, the porous electrode 79 functions as an oxygen reference electrode serving as the reference for detection of the concentration of oxygen in the exhaust gas.

The sensor controller detects an electromotive force Vs generated between the porous electrode 77 and the porous electrode 79 of the oxygen concentration detection cell 81 and compares the detected electromotive force Vs with a predetermined reference voltage Va. Based on the comparison results, the sensor controller controls the magnitude and direction of the pumping current Ip flowing between the porous electrode 85 and the porous electrode 87 of the oxygen pump cell 89. The oxygen pump cell 89 thereby pumps oxygen into or out of the gas measurement chamber 91.

Then the sensor controller detects the pumping current Ip flowing between the porous electrode 85 and the porous electrode 87 of the oxygen pump cell 89.

The reference voltage Va that is compared with the electromotive force Vs when the concentration of oxygen is detected is set in advance. Specifically, when the concentration of oxygen is detected, operation of the oxygen pump cell 89 is controlled such that the electromotive force Vs approaches the reference voltage Va. The sensor controller can thereby compute the concentration of oxygen in the exhaust gas based on the pumping current Ip. The reference voltage Va is set to a voltage value (e.g., 450 mV) at which moisture in the exhaust gas introduced into the gas measurement chamber 91 is not substantially dissociated.

Next, a method for producing the gas sensor element 7 will be described.

First, green insulating sheets for the insulating members 76 and 84 and the insulating substrate 97 of the detection element 71, a green solid electrolyte sheet for the solid electrolyte bodies 75 and 83 of the detection element 71, and green insulating sheets for the insulating substrates 101 and 103 of the heater element 73 are produced.

When the green solid electrolyte sheet for the solid electrolyte bodies 75 and 83 is formed, alumina powder, a butyral resin, etc., are first added to a ceramic powder composed mainly of zirconia, and a solvent mixture is added to the mixture to produce a slurry. The slurry is formed into a sheet shape by a doctor blade method, and then the solvent mixture is volatilized to obtain the green solid electrolyte sheet. Then the green solid electrolyte sheet is cut into rectangular pieces corresponding to the solid electrolyte bodies 75 and 83.

Rectangular through holes corresponding to the plane shapes of the cut green solid electrolyte sheets for the solid electrolyte bodies 75 and 83 are formed in the green insulating sheets for the insulating members 76 and 84. A rectangular through hole corresponding to the shape of the gas passage member 99 is formed in the green insulating sheet for the insulating substrate 97.

To form each green insulating sheet, a butyral resin and dibutyl phthalate are added to a ceramic powder composed mainly of alumina, and a solvent mixture is added to the mixture to produce a slurry. The slurry is formed into a sheet shape by the doctor blade method, and then the solvent mixture is volatilized to thereby prepare the green insulating sheet.

An alumina slurry used as a material that forms the insulating spacer 93 through firing is prepared by adding a butyral resin and dibutyl phthalate to a ceramic powder composed mainly of alumina and then adding a solvent mixture to the mixture.

A porous body slurry used to form green porous bodies that form the diffusion controlling sections 95 and the gas passage member 99 by firing is produced by dispersing 100% by mass of alumina powder, a material to be burnt out by heating (e.g., carbon), and a plasticizer by wet mixing. The plasticizer includes a butyral resin and DBP (dibutyl phthalate).

Next, the heat-generating resistor pattern 105 is formed on the upper surface of the green insulating sheet for the insulating substrate 103. For example, a platinum paste composed mainly of platinum and containing a ceramic (e.g., alumina) is produced as the material of the heat-generating resistor pattern 105. The platinum paste is printed to form the heater pattern.

Patterns for the electrode pads 117 and 119 are formed on the lower surface of the green insulating sheet for the insulating substrate 103 using, for example, a metallized ink such as a platinum metallized ink.

Holes serving as the through holes 181 and 182 are formed in the green insulating sheet for the insulating substrate 103, and the metallized ink is applied to the inner circumferential surfaces of these holes.

The through holes 161 to 172 are formed in the same manner as described above, and the metallized ink is applied to the through holes 161 to 172 in the same manner as described above. Therefore, a redundant description of the through holes 161 to 172 will be omitted.

Next, the green insulating sheet for the insulating substrate 101 is stacked on the upper surface of the green insulating sheet for the insulating substrate 103 so as to cover the heat-generating resistor pattern 105.

Next, the green solid electrolyte sheet for the solid electrolyte body 75 is embedded in the through hole 76a in the green insulating sheet for the insulating member 76. Then an electrode pattern for the porous electrode 77 is formed on the upper surface of the green insulating sheet for the insulating member 76 by screen printing using the platinum metallized ink. A lead pattern for the lead portion 77a is formed by screen printing using a paste prepared by adding alumina to platinum. An electrode pattern for the porous electrode 79 and a lead pattern for the lead portion 79a are formed on the lower surface of the green insulating sheet for the insulating member 76 by screen printing similar to that for the porous electrode 77 and the lead portion 77a on the upper surface.

Then a carbon paste 210 (see FIG. 3C), which is a heat-decomposable paste, is printed on the upper surface of the green insulating sheet for the insulating substrate 101. The carbon paste 210 is disposed in a region that is to be located below the through hole 176 and the periphery of the through hole 176. In the present embodiment, the carbon paste is used as the heat-decomposable paste, but any paste that is decomposed by heat such as theobromine may be used.

A layer that later becomes an insulating layer 220 (see FIG. 2D) is printed, using the alumina slurry, on the upper surface of the green insulating sheet for the insulating substrate 101. This layer is formed in a region in which the carbon paste 210 is not disposed.

Next, the green insulating sheet for the insulating member 76 is stacked on the upper surface of the layer that later becomes the insulating layer 220.

Then a layer that later becomes the insulating spacer 93 is printed on the upper surface of the green insulating sheet for the insulating member 76 using the alumina slurry. First openings are formed in this layer at positions at which the diffusion controlling sections 95 are to be formed, and a second opening is formed in this layer at a position at which the gas measurement chamber 91 is to be formed. The porous body slurry that forms the diffusion controlling sections 95 is disposed within the first openings by printing. The carbon paste is disposed within the second opening serving as the gas measurement chamber 91 by printing. The first openings are connected to the second opening such that gas can flow therebetween.

Next, the green solid electrolyte sheet for the solid electrolyte body 83 is embedded in the through hole 84$a$ in the green insulating sheet for the insulating member 84.

Then an electrode pattern for the porous electrode 85 and a lead pattern for the lead portion 85$a$ are formed on the upper surface of the green insulating sheet for the insulating member 84 by screen printing similar to that for the porous electrodes 77 and 79 and the lead portions 77$a$ and 79$a$. An electrode pattern for the porous electrode 87 and a lead pattern for the lead portion 87$a$ are formed on the lower surface of the green insulating sheet for the insulating member 84 by screen printing similar to that for the porous electrodes 77 and 79 and the lead portions 77$a$ and 79$a$.

Next, the green insulating sheet for the insulating member 84 is stacked on the upper surface of the layer that later becomes the insulating spacer 93. Then the green insulating sheet for the insulating substrate 97 is stacked on the upper surface of the green insulating sheet for the insulating member 84. The porous material slurry is disposed within the through hole corresponding to the space 97$a$ in the green insulating sheet for the insulating substrate 97 in advance by printing. Patterns for the electrode pads 111, 113, and 115 are printed in advance using the metallized ink on the upper surface of the green insulating sheet for the insulating substrate 97.

By stacking these layers in the manner described above, a green stacked body is formed. The green stacked body is pressed at 1 MPa, and a pressed compact is thereby obtained. According to the above description, the pressed compact includes only one green stacked body that later becomes the gas sensor element 7. However, in actuality, the pressed compact includes a plurality of green stacked bodies that later become gas sensor elements 7. Therefore, the pressed compact is cut into a prescribed size, and a plurality of (e.g., 10) green stacked bodies having the same size as the gas sensor elements 7 are thereby obtained. The resin in the green stacked bodies is removed, and the green stacked bodies are subjected to main firing at a firing temperature of 1,500° C. for 1 hour to thereby obtain the gas sensor elements 7.

Next, the step of forming the lead pattern for the lead portion 79$a$ and the step of stacking the green insulating sheet for the insulating member 76 will be described in detail.

Figure 3A:
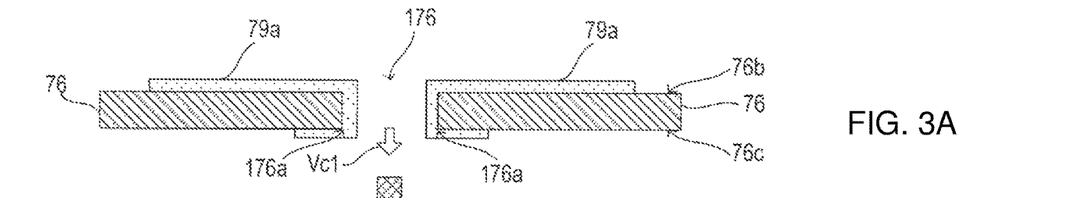
FIGS. 3A to 3E are cross-sectional views showing part of a process for producing the gas sensor element 7.

As shown in FIG. 3A, first, the green insulating sheet for the insulating member 76 is placed such that its surface 76$b$ on which the lead pattern for the lead portion 79$a$ is to be formed faces upward, and vacuum drawing is performed such that a gas flows through the through hole 176 from the upper side of the green insulating sheet to the lower side. An arrow Vc1 shows the flow direction of the gas which flows through the through hole 176 as a result of this vacuum drawing.

In a state in which this vacuum drawing is being performed, the lead pattern for the lead portion 79$a$ is printed on the surface 76$b$. As a result, a portion of the lead pattern for the lead portion 79$a$ printed at the opening of the through hole 176 on the surface 76$b$ side extends from the surface 76$b$ to a surface 76$c$ opposite the surface 76$b$ along an inner circumferential wall of the through hole 176. In this manner, the lead pattern for the lead portion 79$a$ is also formed around an opening of the through hole 176 on the surface 76$c$ side. The lead pattern for the lead portion 79$a$ becomes porous through firing. This allows the lead portion 79$a$ to have the ability to discharge oxygen stored in the porous electrode 79 through the lead portion 79$a$.

Next, the green insulating sheet for the insulating member 76 is placed such that the surface 76$c$ faces upward, and vacuum drawing is performed such that a gas flows through the through hole 176 from the upper side of the green insulating sheet to the lower side. An arrow Vc2 in FIG. 3B shows the flow direction of the gas which flows through the through hole 176 as a result of this vacuum drawing.

Figure 3B:
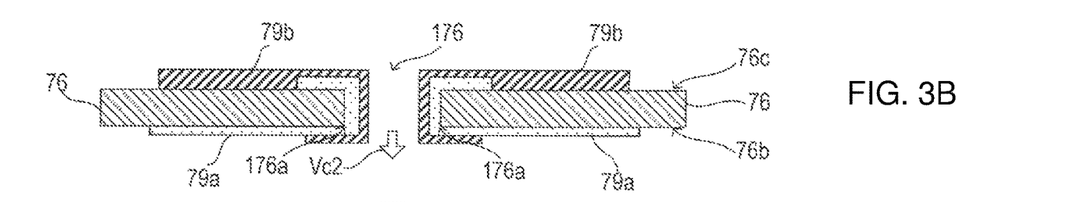

In a state in which this vacuum drawing is being performed, as shown in FIG. 3B, a lead pattern for an output-extracting lead portion 79$b$ is printed on the surface 76$c$. As a result, a portion of the lead pattern for the output-extracting lead portion 79$b$ printed at the opening of the through hole 176 on the surface 76$c$ side extends from the surface 76$c$ to the surface 76$b$ along the inner circumferential wall of the through hole 176. In this manner, the lead pattern for the output-extracting lead portion 79$b$ is also formed around the opening of the through hole 176 on the surface 76$b$ side.

The output-extracting lead portion 79$b$ is provided in order to ensure electrical continuity between the lead portion 79$a$ and the through hole conductor formed in the through hole 176 and is formed to cover the lead portion 79$a$ around the through hole 176. Since the lead portion 79$a$ is porous, the lead portion 79$a$ easily breaks at an edge 176$a$ of the through hole 176 that is located around its opening on the surface 76$c$. Therefore, the output-extracting lead portion 79$b$ needs to be dense enough so as not to break at the edge 176$a$. Accordingly, the lead pattern for the output-extracting lead portion 79$b$ is formed by screen printing using a paste that becomes denser than the lead portion 79$a$ through firing.

Figure 3C:
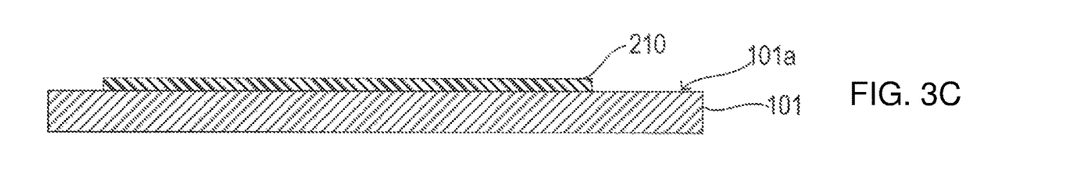
Figure 3D:
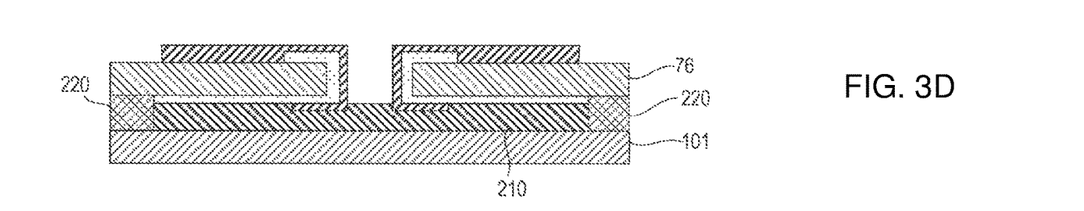

Next, as shown in FIG. 3C, the carbon paste 210 is printed on a surface 101$a$ of the green insulating sheet for the insulating substrate 101, on which surface 101$a$ the insulating member 76 is to be stacked. The carbon paste 210 is disposed in a region that is to face the through hole 176 when the green insulating sheet for the insulating member 76 is stacked and in the periphery of this region. Then the alumina paste that later becomes the insulating layer 220 (see FIG. 3D) is printed on the surface 101$a$ of the green insulating sheet for the insulating substrate 101. The alumina paste is disposed in a region other than the region in which portion the carbon paste 210 has been disposed.

Next, as shown in FIG. 3D, the green insulating sheet for the insulating member 76 is stacked on the upper surface of the layer that later becomes the insulating layer 220.

Figure 3E:
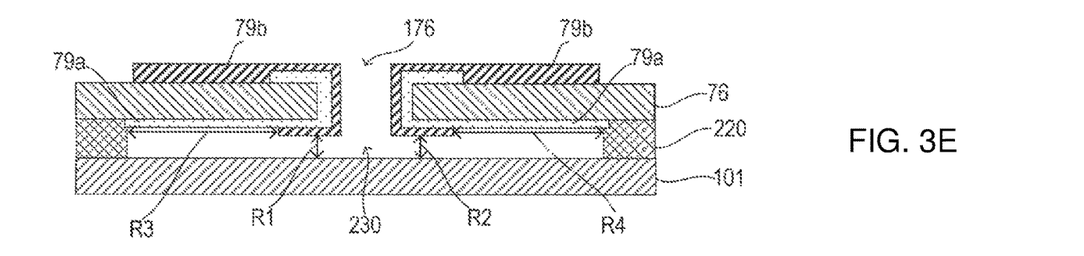

The green stacked body described above is thereby obtained and then fired. As a result, as shown in FIG. 3E, the carbon paste 210 sublimes, and a space 230 is formed in the region previously occupied by the carbon paste 210. As shown by arrows R1 and R2, the output-extracting lead portion 79$b$ is spaced apart from the insulating substrate 101. As shown by arrows R3 and R4, the lead portion 79$a$ has a section exposed to the space 230.

The gas sensor element 7 formed as described above includes the gas measurement chamber 91, the oxygen pump cell 89, the oxygen concentration detection cell 81, the lead portion 79$a$, and the output-extracting lead portion 79$b$.

The exhaust gas is introduced into the gas measurement chamber 91. The oxygen pump cell 89 includes the oxygen ion conductive solid electrolyte body 83 and the pair of porous electrodes 85 and 87 formed on the upper and lower surfaces of the solid electrolyte body 83. The oxygen pump cell 89 pumps oxygen into or out of the exhaust gas introduced into the gas measurement chamber 91 when the pumping current Ip flows between the pair of porous electrodes 85 and 87.

The oxygen concentration detection cell 81 includes the oxygen ion conductive solid electrolyte body 75, the porous electrode 77, and the porous electrode 79 having oxygen permeability. The porous electrode 77 is exposed to the gas measurement chamber 91, and the oxygen concentration detection cell 81 generates an electromotive force Vs corresponding to the difference in oxygen concentration between the porous electrode 77 and the porous electrode 79. The solid electrolyte body 75 is disposed within the through hole 76a formed in the insulating member 76. The porous electrode 77 is formed on the upper surface of the solid electrolyte body 75. The porous electrode 79 is formed on the lower surface of the solid electrolyte body 75.

The lead portion 79a having oxygen permeability is formed on the lower surface of the insulating member 76 such that the lead portion 79a extends from the porous electrode 79 to the through hole 176 formed in the insulating member 76 and further extends from the lower surface of the insulating member 76 through the through hole 176 to the upper surface of the insulating member 76 so as to cover the inner circumferential wall of the through hole 176 and a portion of the upper surface around the through hole 176.

The output-extracting lead portion 79b is formed so as to extend from the upper surface of the insulating member 76 through the through hole 176 to the lower surface of the insulating member 76 so as to cover the lead portion 79a along the inner circumferential wall of the through hole 176 and so as to cover a portion of the lower surface around the through hole 176.

The gas sensor element 7 further includes the insulating substrate 101 and the insulating layer 220. The insulating substrate 101 and the insulating layer 220 are disposed below the lower surface of the insulating member 76 with the space 230 formed between the insulating substrate 101 and the lower surface of the insulating member 76 so as to extend below the through hole 176 and the periphery of the through hole 176. In the gas sensor element 7, the lead portion 79a has the section exposed to the space 230 on the lower side of the insulating member 76. The output-extracting lead portion 79b is spaced apart from the insulating substrate 101 with the space 230 sandwiched therebetween, and the lead portion 79a is in communication with the outside of the gas sensor element 7 through the space 230.

Figure 4:
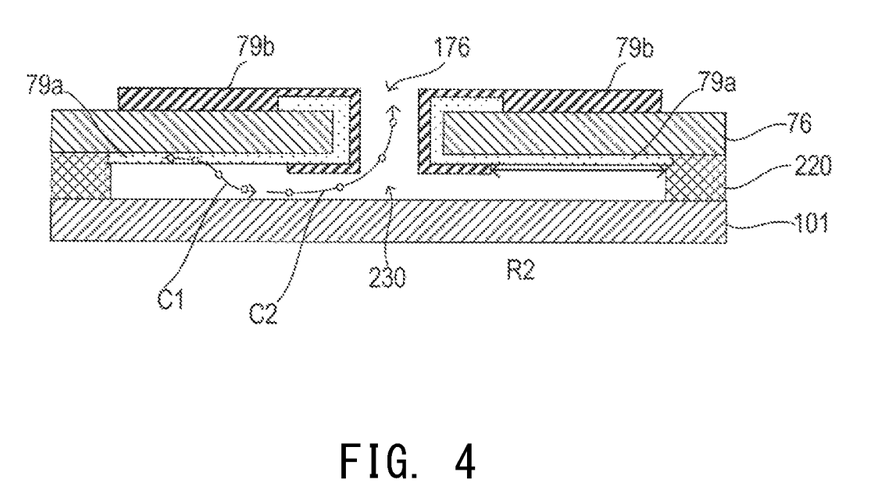
FIG. 4 is a cross-sectional view around a through hole 176, showing flow of oxygen.

As described above, in the gas sensor element 7, the lead portion 79a has the section exposed to the space 230. Therefore, as shown by an arrow C1 in FIG. 4, oxygen stored in the porous electrode 79 can be released into the space 230 through the lead portion 79a connected to the porous electrode 79. In the gas sensor element 7, the output-extracting lead portion 79b is spaced apart from the insulating substrate 101. Therefore, as shown by an arrow C2 in FIG. 4, the oxygen released into the space 230 from the lead portion 79a can flow to the through hole 176 and can be discharged to the outside of the gas sensor element 7 through the through hole 176.

As a result, the gas sensor element 7 can prevent a decrease in the amount of oxygen discharged from the through hole 176. Therefore, the gas sensor element 7 can suppress fluctuations in the oxygen concentration in the porous electrode 79, to thereby improve the stability of the characteristics of the gas sensor element 7.

The exhaust gas corresponds to the gas under measurement in the claims appended hereto, and the gas measurement chamber 91 corresponds to the measurement chamber in the claims. The solid electrolyte body 83 corresponds to the first solid electrolyte body in the claims, and the porous electrodes 85 and 87 correspond to the pair of pumping electrodes in the claims. The oxygen pump cell 89 corresponds to the pumping cell in the claims.

The insulating member 76 and the solid electrolyte body 75 correspond to the plate-shaped cell member in the claims appended hereto, and the solid electrolyte body 75 corresponds to the second solid electrolyte body in the claims. The porous electrode 77 corresponds to the detection electrode in the claims, and the porous electrode 79 corresponds to the reference electrode in the claims. The oxygen concentration detection cell 81 and the insulating member 76 correspond to the oxygen concentration detection cell in the claims.

The through hole 176 corresponds to the through hole in the claims appended hereto. The lead portion 79a corresponds to the first lead portion in the claims, and the output-extracting lead portion 79b corresponds to the second lead portion in the claims.

The space 230 corresponds to the space in the claims appended hereto. The insulating substrate 101 and the insulating layer 220 corresponds to the insulating layer in the claims, and the insulating substrate 101 corresponds to the lower insulating layer in the claims.

The embodiment of the present disclosure has been described above, but the present disclosure is not limited to the above embodiment and can be embodied in various other forms.

For example, in the above embodiment, the oxygen sensor including the gas measurement chamber 91, the oxygen pump cell 89, and the oxygen concentration detection cell 81 is shown. The present disclosure may be applied to an NOx sensor that includes an oxygen pump cell and an oxygen concentration detection cell and detects the concentration of nitrogen oxides.

In the embodiment shown above, the plate-shaped cell member includes the insulating member 76 and the solid electrolyte body 75 disposed within the through hole 76a, but the plate-shaped cell member may be composed of the solid electrolyte body 75 alone.

A function of one component in the above embodiments may be embodied by a plurality of components, or functions of a plurality of components may be embodied by one component. Part of the configurations of the above embodiments may be omitted. At least part of the configuration of each of the above embodiments may be added to or replaced with the configurations of other embodiments.

The invention has been described in detail with reference to the above embodiments. However, the invention should not be construed as being limited thereto. It should further be apparent to those skilled in the art that various changes in form and detail of the invention as shown and described above may be made. It is intended that such changes be included within the spirit and scope of the claims appended hereto.

This application is based on Japanese Patent Application No. 2016-153021 filed Aug. 3, 2016, incorporated herein by reference in its entirety.

What is claimed is:

1. A gas sensor element comprising:
   a measurement chamber into which a gas under measurement is introduced;

a pumping cell including a first solid electrolyte body having oxygen ion conductivity and a pair of pumping electrodes formed on the first solid electrolyte body, the pumping cell pumping oxygen into or out of the gas under measurement that has been introduced into the measurement chamber when a pumping current flows between the pair of pumping electrodes;

an oxygen concentration detection cell including a plate-shaped cell member which includes at least a second solid electrolyte body having oxygen ion conductivity, a detection electrode formed on an upper surface of the second solid electrolyte body, and a reference electrode having oxygen permeability and formed on a lower surface of the second solid electrolyte body, the detection electrode being exposed to the measurement chamber, the oxygen concentration detection cell generating an electromotive force corresponding to a difference in oxygen concentration between the detection electrode and the reference electrode;

a first lead portion having oxygen permeability and formed on a lower surface of the plate-shaped cell member so as to extend from the reference electrode to a through hole formed in the plate-shaped cell member and further extend from the lower surface of the plate-shaped cell member through the through hole to an upper surface of the plate-shaped cell member so as to cover an inner circumferential wall of the through hole and a portion of the upper surface around the through hole; and a second lead portion formed so as to extend from the upper surface of the plate-shaped cell member through the through hole to the lower surface of the plate-shaped cell member so as to cover the first lead portion along the inner circumferential wall of the through hole and a portion of the lower surface around the through hole, wherein an insulating substrate is disposed below the plate-shaped cell member so as to face the plate-shaped cell member and thereby form a space along the lower surface of the plate-shaped cell member extending across the through hole and a periphery of the through hole;

the first lead portion has a section exposed to the space below the lower surface of the plate-shaped cell member;

the second lead portion is spaced apart from the insulating substrate with the space therebetween;

the first lead portion is in communication with the outside of the gas sensor element via the space and the through hole;

the gas sensor element is configured such that oxygen accumulating in the reference electrode that flows to the outside of the gas sensor flows through the first lead portion;

an insulating layer is disposed between the insulating substrate and the plate-shaped cell member;

a surface of the insulating layer faces the space; and a part of the first lead portion on the lower surface of the plate-shaped cell member, which is not covered by the second lead portion and which does not face the space, is in contact with the insulating layer.

2. The gas sensor element according to claim 1, wherein a density of the first lead portion is lower than a density of the second lead portion.

3. The gas sensor element according to claim 1, wherein a first segment of the first lead portion extends along the lower surface of the plate-shaped cell member for a first distance, and the first segment is not covered by the second lead portion.

4. The gas sensor element according to claim 1, wherein the oxygen stored in the reference electrode is released into the space through the first lead portion and then flows through the through hole to be discharged to the outside of the sensor element.

5. The gas sensor element according to claim 1, wherein the insulating layer has a surface abutting the plate-shaped cell member, a surface abutting the insulating substrate, and the surface exposed to the space.

6. The gas sensor element according to claim 1, wherein a part of the first lead portion on the lower surface of the plate-shaped cell member, which is not covered by the second lead portion, and which is not exposed to the space, is clipped between the insulating layer and the plate-shaped cell member.

7. The gas sensor element according to claim 6, wherein the insulating layer has a surface abutting the plate-shaped cell member, a surface abutting the insulating substrate, and the surface exposed to the space.

8. A gas sensor element comprising:

a measurement chamber into which a gas under measurement is introduced;

a pumping cell including a first solid electrolyte body having oxygen ion conductivity and a pair of pumping electrodes formed on the first solid electrolyte body, the pumping cell pumping oxygen into or out of the gas under measurement that has been introduced into the measurement chamber when a pumping current flows between the pair of pumping electrodes;

an oxygen concentration detection cell including a plate-shaped cell member which includes at least a second solid electrolyte body having oxygen ion conductivity, a detection electrode formed on an upper surface of the second solid electrolyte body, and a reference electrode having oxygen permeability and formed on a lower surface of the second solid electrolyte body, the detection electrode being exposed to the measurement chamber, the oxygen concentration detection cell generating an electromotive force corresponding to a difference in oxygen concentration between the detection electrode and the reference electrode;

a first lead portion having oxygen permeability and formed on a lower surface of the plate-shaped cell member so as to extend from the reference electrode to a through hole formed in the plate-shaped cell member and further extend from the lower surface of the plate-shaped cell member through the through hole to an upper surface of the plate-shaped cell member so as to cover an inner circumferential wall of the through hole and a portion of the upper surface around the through hole; and a second lead portion formed so as to extend from the upper surface of the plate-shaped cell member through the through hole to the lower surface of the plate-shaped cell member so as to cover the first lead portion along the inner circumferential wall of the through hole and a portion of the lower surface around the through hole, wherein an insulating substrate is disposed below the plate-shaped cell member so as to face the plate-shaped cell member and thereby form a space along the lower surface of the plate-shaped cell member extending across the through hole and a periphery of the through hole;

the first lead portion has a section exposed to the space below the lower surface of the plate-shaped cell member;

the second lead portion is spaced apart from the insulating substrate with the space therebetween;

the first lead portion is in communication with the outside of the gas sensor element via the space and the through hole; and a first segment of the first lead portion extends along the lower surface of the plate-shaped cell member for a first distance, and the first segment is not covered by the second lead portion.

9. The gas sensor element according to claim 8, wherein oxygen stored in the reference electrode flows through the first lead portion to be discharged to the outside of the gas sensor element.

10. The gas sensor element according to claim 8, wherein the oxygen stored in the reference electrode is released into the space through the first lead portion and then flows through the through hole to be discharged to the outside of the sensor element.

11. The gas sensor element according to claim 8, wherein a density of the first lead portion is lower than a density of the second lead portion.

12. The gas sensor element according to claim 8, wherein a part of the first lead portion on the lower surface of the plate-shaped cell member, which is not covered by the second lead portion, and which is not exposed to the space, abuts an insulating layer, and wherein the insulating layer is disposed between the plate-shaped cell member and the insulating substrate to partially define the space.

13. The gas sensor element according to claim 12, wherein the insulating layer has a surface abutting the plate-shaped cell member, a surface abutting the insulating substrate, and a surface exposed to the space.

14. The gas sensor element according to claim 13, wherein the gas sensor element is configured such that oxygen accumulating in the reference electrode that flows to the outside of the sensor flows through the first lead portion.

15. The gas sensor element according to claim 8, wherein a part of the first lead portion on the lower surface of the plate-shaped cell member, which is not covered by the second lead portion, and which is not exposed to the space, is clipped between an insulating layer and the plate-shaped cell member, and wherein the insulating layer is disposed between the plate-shaped cell member and the insulating substrate to partially define the space.

16. The gas sensor element according to claim 8, wherein the insulating layer has a surface abutting the plate-shaped cell member, a surface abutting the insulating substrate, and a surface exposed to the space.

17. The gas sensor element according to claim 16, wherein the gas sensor element is configured such that oxygen accumulating in the reference electrode that flows to the outside of the sensor flows through the first lead portion.

* * * * *